(12) United States Patent
Hausner et al.

(10) Patent No.: US 7,514,885 B2
(45) Date of Patent: Apr. 7, 2009

(54) METHODS AND SYSTEMS FOR MEDICAL IMAGING

(75) Inventors: Danny Hausner, Haifa (IL); Yaron Hefetz, Herzeliya (IL)

(73) Assignee: General Electric Company, Schenectady, NY (US)

(*) Notice: Subject to any disclaimer, the term of this patent is extended or adjusted under 35 U.S.C. 154(b) by 667 days.

(21) Appl. No.: 11/075,432

(22) Filed: Mar. 8, 2005

(65) Prior Publication Data

US 2006/0202650 A1    Sep. 14, 2006

(51) Int. Cl.
*H02P 1/00* (2006.01)
(52) U.S. Cl. .................. 318/268; 378/117; 212/284; 212/320; 212/322
(58) Field of Classification Search ............ 250/363.02; 378/117; 318/268, 432; 212/284, 320, 322
See application file for complete search history.

(56) References Cited

U.S. PATENT DOCUMENTS

| | | | | |
|---|---|---|---|---|
| 5,550,890 A | * | 8/1996 | Anderson | 378/136 |
| 5,554,848 A | * | 9/1996 | Hermony et al. | 250/363.05 |
| 6,088,425 A | * | 7/2000 | Ono | 378/117 |
| 6,973,158 B2 | * | 12/2005 | Besson | 378/16 |
| 7,087,903 B2 | * | 8/2006 | Balan et al. | 250/363.02 |
| 7,116,749 B2 | * | 10/2006 | Besson | 378/16 |
| 7,194,062 B2 | * | 3/2007 | Balan et al. | 378/15 |
| 2003/0128801 A1 | | 7/2003 | Eisenberg et al. | |
| 2004/0120462 A1 | | 6/2004 | Wilson et al. | |
| 2008/0086052 A1 | * | 4/2008 | Hsieh | 600/427 |

FOREIGN PATENT DOCUMENTS

WO   WO 2006/018763 A1   2/2006

* cited by examiner

*Primary Examiner*—Bentsu Ro
*Assistant Examiner*—Antony M Paul
(74) *Attorney, Agent, or Firm*—The Small Patent Law Group; Dean D. Small (57) ABSTRACT

Methods and systems for medical imaging are provided. The system includes a gantry assembly having a stator, a first rotor rotatably coupled to the stator, the first rotor configured to rotate about an examination axis at a first rotational speed, and a second rotor rotatably coupled to at least one of the stator and the first rotor, the second rotor configured to rotate about the examination axis at the first and a second rotational speed, the second rotational speed being greater than the first rotational speed, the first and second rotors configured to be locked in position with respect to each other during rotation at the first rotational speed, the first rotor configured to be locked in position with respect to the stator during rotation of the second rotor at the second rotational speed.

22 Claims, 6 Drawing Sheets

METHODS AND SYSTEMS FOR MEDICAL IMAGING

BACKGROUND OF THE INVENTION

This invention relates generally to medical imaging systems, and more particularly to methods and systems for multi-modality medical imaging.

At least some known multi-modality medical imaging systems use a multi head nuclear medicine (NM) or gamma camera scanner and a computed tomography (CT) or X-ray scanner in tandem. A single patient table may be used to position the patient within each modality scanner without having to readjust the position of the patient on the bed or translate the bed between scanners. Separate gantries are used for each scanner to provide a rotational speed for the NM camera scanner and a different relatively faster rotational speed for the CT scanner. However, having two imaging detector gantries in tandem requires a large footprint and consequently a large imaging room. Using two separate gantries in the imaging system is also a large cost factor for supplying the system and maintaining it.

BRIEF DESCRIPTION OF THE INVENTION

In one embodiment, a gantry assembly for medical imaging is provided. The gantry assembly includes a stator, a first rotor rotatably coupled to the stator wherein the first rotor is configured to rotate about an examination axis at a first rotational speed. The gantry assembly also includes a second rotor rotatably coupled to at least one of the stator and the first rotor wherein the second rotor is configured to rotate about the examination axis at the first rotational speed and a second rotational speed, the second rotational speed being greater than the first rotational speed, the first and second rotors configured to be locked in position with respect to each other during rotation at the first rotational speed, the first rotor configured to be locked in position with respect to the stator during rotation of the second rotor at the second rotational speed.

In another embodiment, a medical imaging system is provided. The system includes a gantry having a stator, a first rotor including at least one gamma camera wherein the first rotor rotatably coupled to the stator through a first main gantry bearing and the first rotor is configured to rotate about an examination axis at a first rotational speed. The gantry also includes a second rotor including an x-ray source and an x-ray detector wherein the second rotor is selectably rotatably coupled to at least one of the stator and the first rotor, the second rotor is configured to rotate about the examination axis at a second rotational speed, the second rotational speed being greater than the first rotational speed, the first and second rotors configured to be locked in position with respect to each other during rotation at the first rotational speed, the first rotor configured to be locked in position with respect to the stator during rotation of the second rotor at the second rotational speed. The system also includes a drive system coupled to the gantry, the drive system configured to rotatably drive the first rotor and the second rotor at a first rotational speed when the first and second rotors are rotationally coupled together during a first portion of a scan, the drive system configured to rotatably drive the second rotor only at a second rotational speed when the first and second rotors are rotationally separated from each other during a second portion of the scan, the second rotational speed being greater than the first rotational speed.

In yet another embodiment, a method of imaging a patient using a dual modality imaging system is provided. The method includes coupling a gamma camera rotor to a stator, coupling a computed tomography (CT) rotor to at least one of the gamma camera rotor and the stator, and rotating the gamma camera rotor about the patient at a first rotational speed during a first portion of a scan, rotating the CT rotor about the patient at a second rotational speed during a second portion of the scan wherein the second rotational speed is different than the first rotational speed, and generating an image of the patient using the first and second portions of the scan.

DETAILED DESCRIPTION OF THE INVENTION

Figure 1:
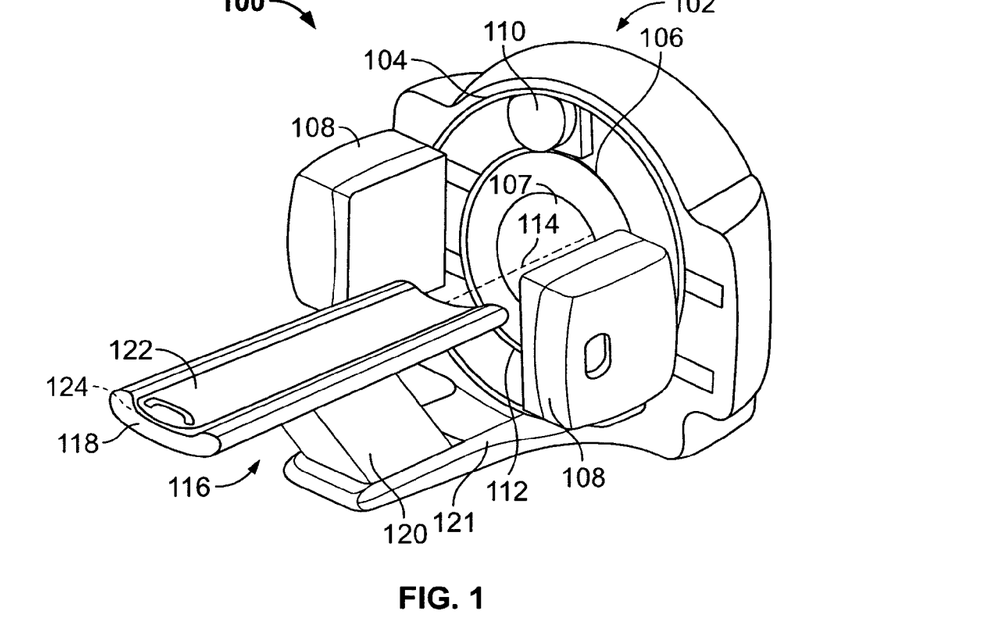
FIG. 1 is a perspective view of an exemplary embodiment of a multi-modality medical imaging system.

FIG. 1 is a perspective view of an exemplary embodiment of a multi-modality medical imaging system 100 including an integrated gantry 102 that includes a radially outer rotor 104 and a radially inner rotor 106 concentrically oriented about a gantry central bore 107. Rotor 104 is configured to support one or more nuclear medicine (NM) cameras 108, such as, but not limited to gamma cameras, SPECT detectors, and/or PET detectors. Rotor 106 is configured to support an x-ray source 110 and a substantially diametrically opposed x-ray detector 112. Rotors 104 and 106 are further configured to rotate co-axially about an examination axis 114. A patient table 116 may include a bed 118 slidingly coupled to a bed support system 120, which may be coupled directly to a floor or may be coupled to gantry 102 through a base 121 coupled to gantry 102. Bed 118 may include a stretcher 122 slidingly coupled to an upper surface 124 of bed 118. Patient table 116 is configured to facilitate ingress and egress of a patient (not shown) into an examination position that is substantially aligned with examination axis 114. During an imaging scan, patient table 116 may be controlled to move bed 118 and/or stretcher 122 axially into and out of bore 107.

Figure 2:
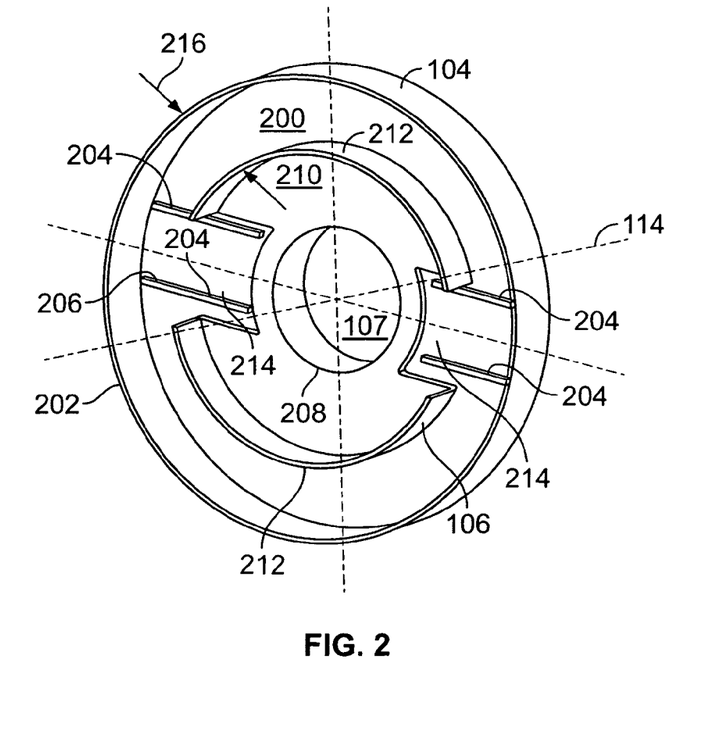
FIG. 2 is a cutaway perspective view of an exemplary embodiment of the rotors shown in FIG. 1.

FIG. 2 is a cutaway perspective view of an exemplary embodiment of rotors 104 and 106 (shown in FIG. 1). In the exemplary embodiment, rotor 104 includes a planar disk 200 having a circumferential support rim 202 extending axially therefrom. Disk 200 includes a pair of camera rails 204 for each NM camera rotor 104 is configured to carry. In the exemplary embodiment, disk 200 includes two pairs of camera rails 204 that extend chordwise from a first end 206 proximate rim 202 toward an outer periphery 208 of bore 107. Camera rails 204 are configured to slidably engage NM cameras 108 to permit NM cameras 108 to be moved radially toward and away from examination axis 114. Rotor 106 includes a disk 210 having a support rim 212 extending at least partially about a radially outer periphery of disk 210. Disk 210 includes a cutout portion 214 for each NM camera rotor 104 is configured to carry. In the exemplary embodiment, support rim 212 extends between cutouts 214. Cutouts 214 are sized to accommodate a width of NM cameras 108 such that when NM cameras 108 are in a radially inner position, NM cameras 108 fit between support rims 212. Support rim 202 and support rims 212 are separated by a radial distance 216 that provides sufficient clearance so that when NM cameras 108 are in a radially outer position, rotors 104 and 106 may rotate with respect to each other without interference between rotors 104 and 106.

Figure 3:
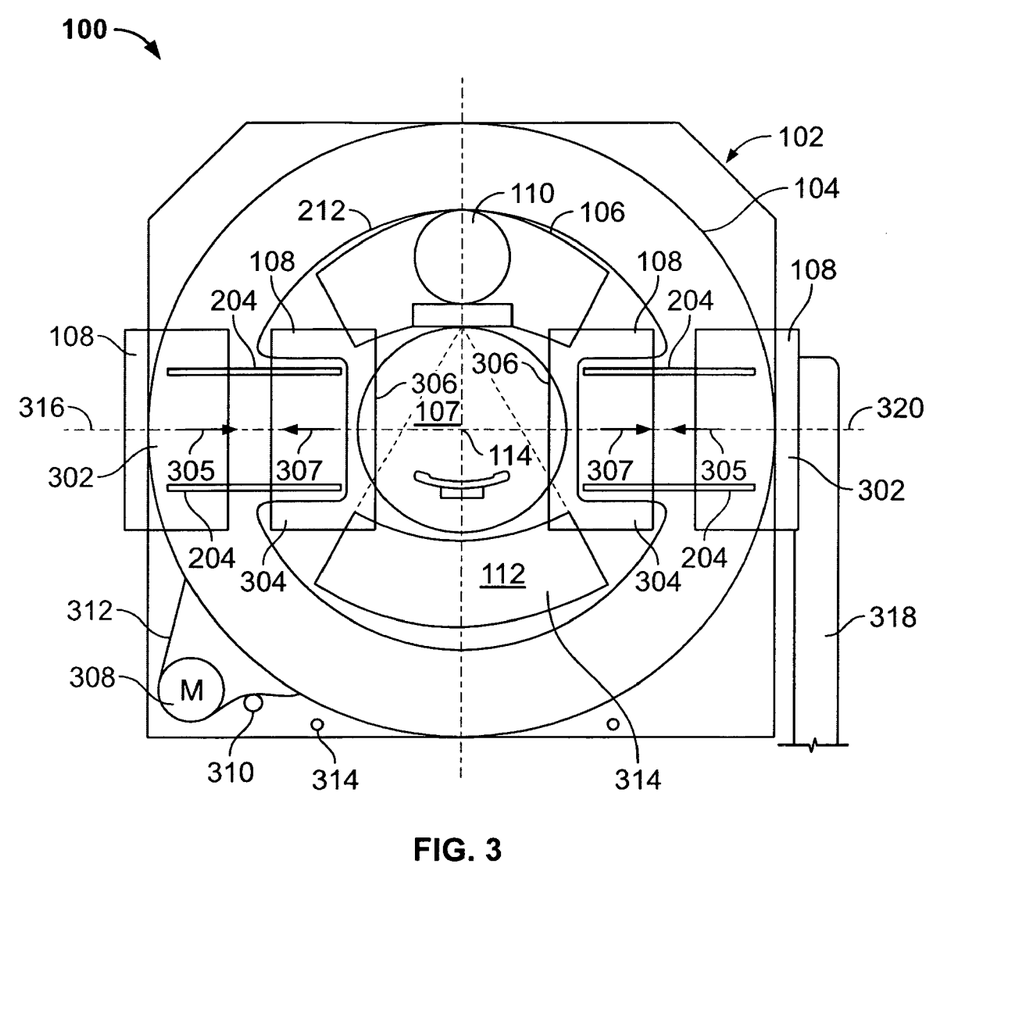
FIG. 3 is a front perspective view of an exemplary embodiment of the multi-modality medical imaging system shown in FIG. 1.

FIG. 3 is a front perspective view of an exemplary embodiment of multi-modality medical imaging system 100 (shown in FIG. 1). In the exemplary embodiment, NM cameras 108 are illustrated in a fully radially out position 302 and in a fully radially in position 304. NM cameras 108 may be moved between positions 302 and 304 by moving NM cameras 108 along camera rails 204 in a radially in direction 305 or radially out direction 307. In position 304, a face 306 of NM cameras 108 is located proximate bore 107 such that a patient aligned with axis 114 may be readily scanned. In position 302, faces 306 are retracted away from bore 107 sufficiently to provide clearance between support rim 212 and faces 306. In the exemplary embodiment, multi-modality medical imaging system 100 includes a motor 308, an idler 310 and an drive belt 312 operatively coupled to rotor 106 to provide rotational power to drive rotor 106 and rotor 104 in rotation about examination axis 114. In various alternative embodiments, multi-modality medical imaging system 100 includes a direct drive or gear drive. An engagement point 314 may be used to couple base 121 to gantry 102. In various embodiments, it may be desirable to tilt gantry 102 about a horizontal axis 316 of gantry 102. A tilt mechanism 318 rotatably couples to gantry 102 through a pivot 320 substantially aligned with axis 316. Gantry 102 may be configured to rotate about axis 316 in a manual or powered mode.

Figure 4:
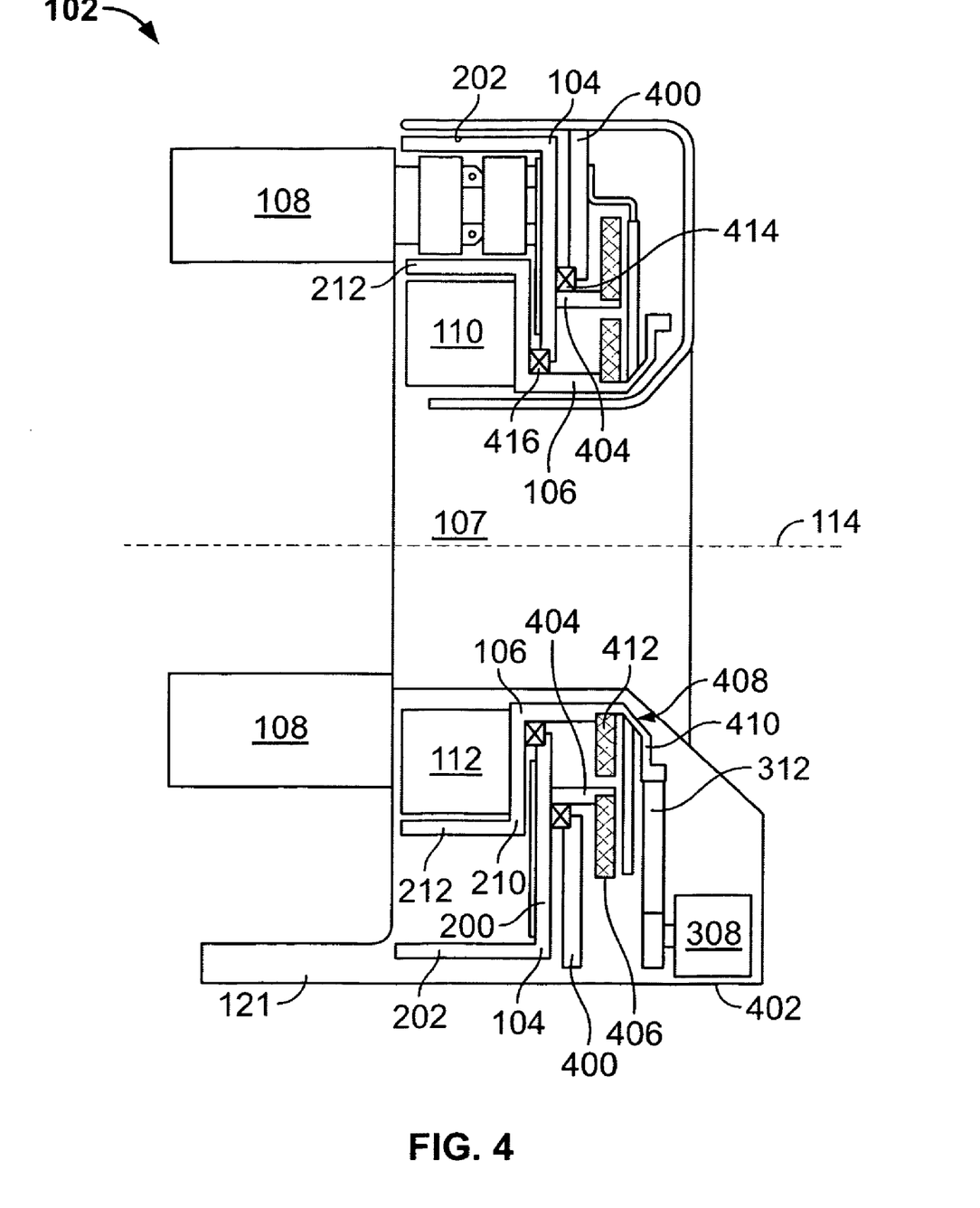
FIG. 4 is a side enlarged perspective view, with covers removed, of an exemplary embodiment of the gantry shown in FIG. 1.

FIG. 4 is a side enlarged perspective view with covers removed of an exemplary embodiment of gantry 102 (shown in FIG. 1). Gantry 102 includes a stationary stator 400 fixedly coupled to a structurally stable base member 402. Stator 400 extends circumferentially about bore 107. Rotor 104 includes disk 200 and support rim 202 and also includes a slip ring support rim 404 that extends axially away from disk 200. A distal end of slip ring support rim 404 is coupled to a first slip ring 406 of a slip ring assembly 408. Slip ring portion 406 is electrically coupled to a brush assembly 410 for transmitting signals between rotor 104 and stator 400. Brush assembly 410 is also electrically coupled to a second slip ring 412 of slip ring assembly 408. Second slip ring 412 and brush assembly 410 are configure to transmit signals between rotor 106 and stator 400.

Rotor 104 is coupled to stator 400 through a main bearing 414 that supports rotor 104 directly and rotor 106 through a secondary bearing 416 coupled between rotor 104 and rotor 106. Secondary bearing 416 permits rotor 106 to rotate with respect to rotor 104 and main bearing 414 permits rotor 104 to rotate with respect to stator 400.

In operation, a nuclear medicine (NM) portion of a scan may be conducted with rotor 104 rotationally locked to rotor 106. The NM portion of the scan may be conducted at a relatively low rotational speed, for example, three rotations per minutes. A computed tomography (CT) or x-ray portion of the scan may be conducted at a relatively higher rotational speed, for example three rotations per second. During a CT portion of the scan, the mass of NM cameras 108 substantially prohibits NM cameras 108 from being rotated at the relatively higher speed. Rotating NM cameras 108 at the relatively higher speeds would require massive rotation support components, for example, base 402, bearing 414, disk 200, and support rim 202. Instead, NM cameras 108 are parked in radially outer position 302 and rotor 104 is locked to stator 400. Motor 308 drives rotor 106 through belt 312 at the relatively high rotational speed during the CT portion of the scan and rotor 106 rotates about examination axis 114 using secondary bearing 416.

Figure 5:
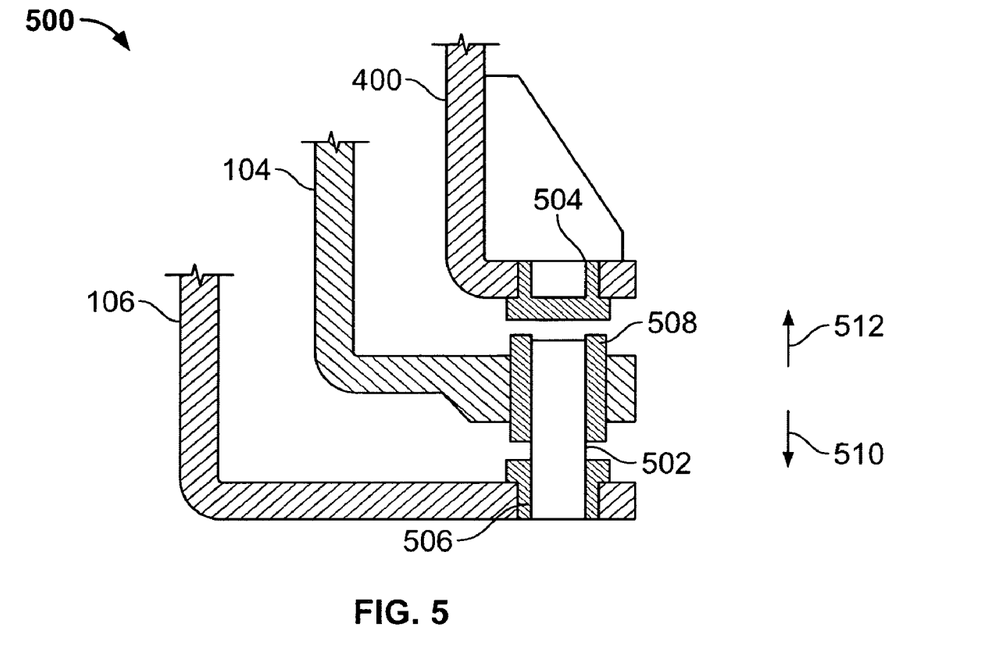
FIG. 5 is a perspective view of an exemplary switching system that may be used with the integrated gantry shown in FIG. 1.

FIG. 5 is a perspective view of an exemplary switching system 500 that may be used with integrated gantry 102 (shown in FIG. 1). Switching system 500 includes a movable pin 502 configured to engage a socket 504 on stator 400 and a socket 506 on rotor 106. Pin 502 may be electrically positionable using, for example, a solenoid coil 508 with pin 502 being a solenoid slug. Pin 502 may also be movable using a mechanical linkage (not shown).

In operation, during a NM scan, pin 502 is controlled to move to an NM position 510 wherein rotors 104 and 106 are rotationally locked together through pin 502. Rotor 106 is coupled to motor 308 through belt 312 such that motor 308 controls the speed of rotation of rotor 106 and rotor 104. When rotors 104 and 106 are locked together in NM scan position 510, motor 308 is controlled to rotate rotors 104 and 106 only in a relatively slow NM scan speed. Switching pin 502 to an x-ray position 512 locks rotor 104 to stator 400 and releases rotor 106 to rotate independent of rotor 104. When pin 501 is in X-ray position 512, rotor 106 is free to be rotated by motor 308 at a rotation speed for an X-ray scan, such as a CT scan. Alternatively, two separate locking mechanisms may be used: the first for locking rotor 104 to rotor 106, the second to lock rotor 106 to the stator 400.

Figure 6:
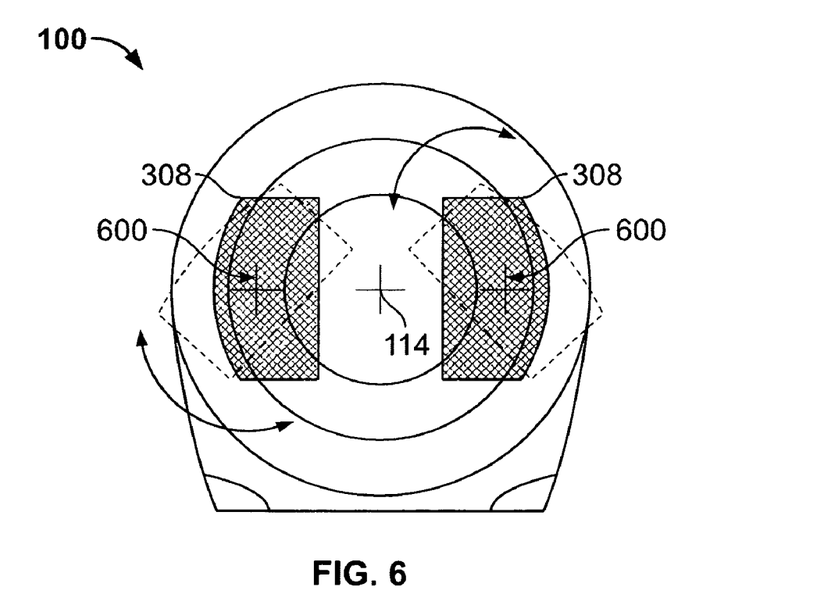
FIG. 6 is a front perspective view of an exemplary embodiment of the multi-modality medical imaging system shown in FIG. 1.

FIG. 6 is a front perspective view of an exemplary embodiment of multi-modality medical imaging system 100 (shown in FIG. 1). NM cameras 108 may be configured to swivel about a pivot axis 600 such that NM cameras 108 may be oriented at ninety degrees with respect to each other. Moving NM cameras 108 radially inwardly until a corner of each NM camera contacts or nearly contacts the other, orients NM cameras in an L-mode configuration. Accordingly, NM cameras 108 may be switched from an H-mode configuration to an L-mode configuration by swiveling NM cameras 108 about axis 600 and moving NM cameras toward each other until a corner of each NM camera contacts or nearly contacts the other. NM cameras 108 may be swiveled at least 180 degrees about axis 600 for maintenance to NM cameras 108 and/or conducting a scan.

Figure 7:
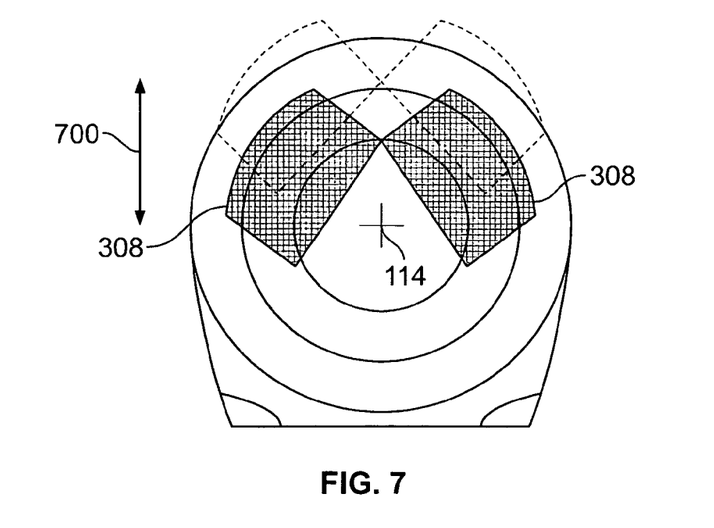
FIG. 7 is another front perspective view of an exemplary embodiment of the multi-modality medical imaging system shown in FIG. 1.

FIG. 7 is another front perspective view of an exemplary embodiment of multi-modality medical imaging system 100 (shown in FIG. 1). In the exemplary embodiment, NM cameras 108 are configured to be controlled to move in a lateral direction 700 that is substantially perpendicular to radially in and radially out directions 305 and 307. Movement of NM cameras 108, in the L-mode configuration, in lateral direction 700, permits movement of NM cameras 108 in the L-mode configuration toward and away from axis 114 to accommodate scanning a smaller or larger patient and/or conduct a specialized scan requiring motion in lateral direction 700. Alternatively, when NM cameras 108 are in L-Mode and radially outward and in the lower section of their orbit, the weight of NM cameras 108 may be used to prevent rotor 104 from rotating instead of pin 502.

Figure 8:
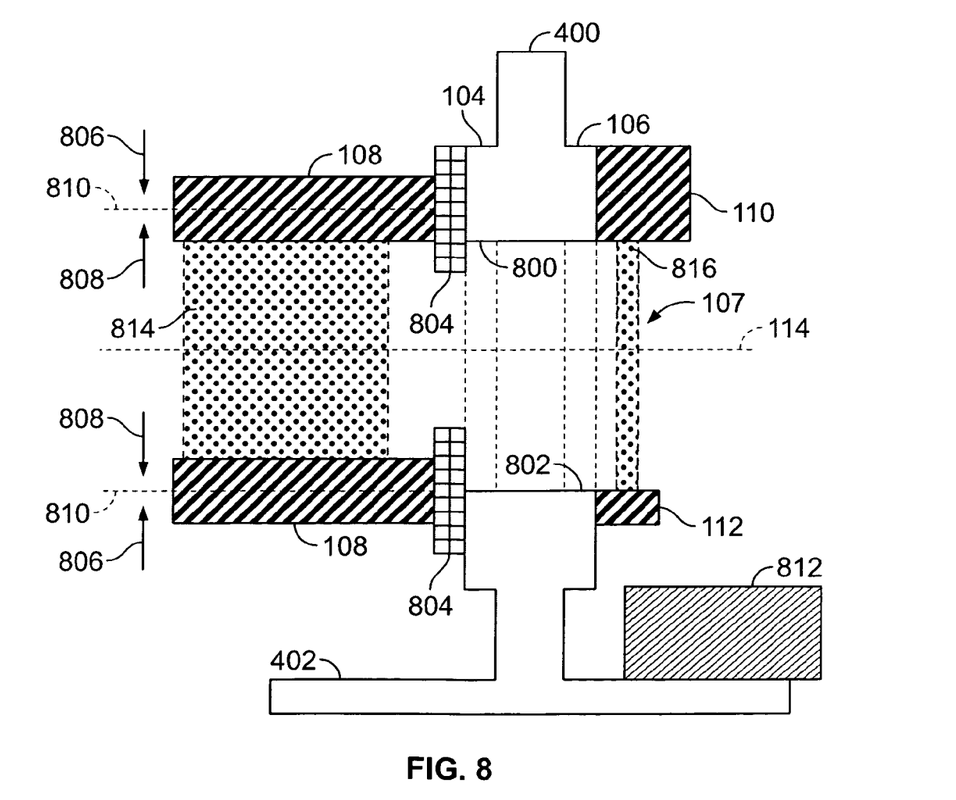
FIG. 8 is a side schematic view of another exemplary embodiment of an exemplary embodiment of the gantry 102 shown in FIG. 1.

FIG. 8 is a side schematic view of another exemplary embodiment of an exemplary embodiment of gantry 102 (shown in FIG. 1). Gantry 102 includes a stationary stator 400 fixedly coupled to a structurally stable base member 402. Stator 400 extends circumferentially about bore 107. Rotor 104 is rotatably coupled to stator 400 through a first bearing 800. Rotor 106 is rotatably coupled to stator 400 through a second bearing 802. Each of rotor 104 and rotor 106 also include a slip ring rotatable portion (not shown) that communicatively engages a slip ring stationary portion (not shown) coupled to stator 400. The slip ring rotatable portion and stationary portions may communicate through electrical contact between the slip ring rotatable portion and stationary portions, or other communication means such as, but, not limited to, optical and/or radio frequency (RF) communication. NM detectors 108 are each coupled to rotor 104 through a swivel and transport mechanism 804 that are configured to move NM detectors 108 in a radially inward direction 806 and a radially outward direction 808. Swivel and transport mechanism 804 also may be configured to move NM detectors 108 in a lateral direction that is perpendicular to radial directions 806 and 808, and examination axis 114. Swivel and transport mechanism 804 is also configured to swivel NM detectors 108 about a swivel axis 810. Combinations of movements in radial directions 806, 808, the lateral direction and about swivel axis 810 permit NM detectors 108 to be controlled in an L-mode configuration, an H-mode configuration, or other modes selected for a particular scanning protocol. A controller 812 controls movement of NM detectors 108 and rotors 104 and 106 during an NM portion of a scan and during an x-ray or CT portion of the scan. Controller 812 receives scan data from NM detectors 108 and x-ray detector 112 during respective portions of the scan, preprocesses the data and forwards the data to a display and/or processor for further processing and/or storage.

In operation, the NM portion of the scan may be conducted with rotor 104 rotationally powered separately from rotor 106. Each rotor may be controlled for each respective portion of the scan independently from the other rotor and may rotate about a respective NM viewing volume 814 and an x-ray viewing volume 816 simultaneously or sequentially during the scan. The NM portion of the scan may be conducted at a relatively low rotational speed, for example, three rotations per minutes. A computed tomography (CT) or x-ray portion of the scan may be conducted at a relatively higher rotational speed, for example three rotations per second. Motor 308 drives rotor 106 through belt 312 at the relatively high rotational speed during the CT portion of the scan. During the NM portion of the scan, a motor (not shown) drives rotor 104 at the relatively slower NM rotational speed. Either rotor may be selectively locked to stator 400 during a portion of the scan that the detectors associated with that rotor are not in use. Each rotor may perform its associated portion of the scan simultaneously with the other rotor when performing its portion of the scan.

Figure 9:
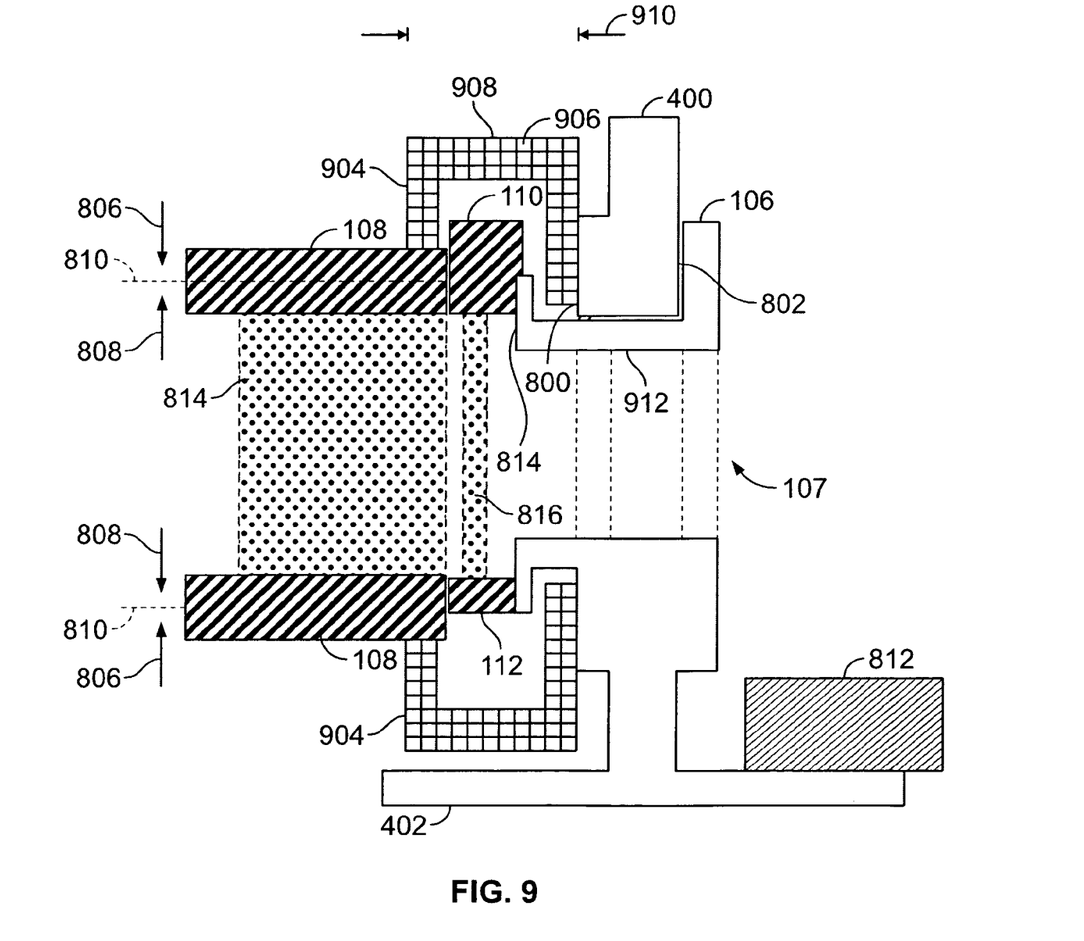
FIG. 9 is a side schematic view of another exemplary embodiment of an exemplary embodiment of gantry shown in FIG. 1.

FIG. 9 is a side schematic view of another exemplary embodiment of an exemplary embodiment of gantry 102 (shown in FIG. 1). Gantry 102 includes a stationary stator 400 fixedly coupled to a structurally stable base member 402. Stator 400 extends circumferentially about bore 107. Rotor 104 is rotatably coupled to stator 400 through a first bearing 800. NM detectors 108 are each coupled to rotor 104 through a swivel and transport mechanism 904 that are configured to move NM detectors 108 in a radially inward direction 806 and a radially outward direction 808. Swivel and transport mechanism 904 also may be configured to move NM detectors 108 in a lateral direction that is perpendicular to radial directions 806 and 808, and examination axis 114. Swivel and transport mechanism 904 is also configured to swivel NM detectors 108 about a swivel axis 810. Combinations of movements in radial directions 806, 808, the lateral direction and about swivel axis 810 permit NM detectors 108 to be controlled in an L-mode configuration, an H-mode configuration, or other modes selected for a particular scanning protocol. Swivel and transport mechanism 904 includes a radially outward extending member 906. A clearance member 908 extends axially away from member 906 a distance 910 that is sufficient to provide clearance for x-ray source 110 and x-ray detector 112, which in the exemplary embodiment are configure to rotate about axis 114 on the same side of stator 400 as NM detectors 108.

Rotor 106 is rotatably coupled to stator 400 through a second bearing 802 and includes a bore clearance member 912 that extends axially through bore 107 from bearing 802 to an x-ray support rim 914 that is configured to couple x-ray source 110 and x-ray detector 112 and transfer the weight loading of x-ray source 110 and x-ray detector 112 to bearing 802. In the exemplary embodiment, NM viewing volume 814 and x-ray viewing volume 816 are axially adjacent because of the configuration of clearance member 908 and bore clearance member 912 that permit the location of NM detectors 108 and x-ray source 110 and x-ray detector 112 on the same side of stator 400.

As described above, each of rotor 104 and rotor 106 also include a slip ring rotatable portion (not shown) that communicatively engages a slip ring stationary portion (not shown) coupled to stator 400. The slip ring rotatable portion and stationary portions may communicate through electrical contact between the slip ring rotatable portion and stationary portions, or other communication means such as, but, not limited to, optical and/or radio frequency (RF) communication.

A controller 812 controls movement of NM detectors 108 and rotors 104 and 106 during an NM portion of a scan and during an x-ray or CT portion of the scan. Controller 812 receives scan data from NM detectors 108 and x-ray detector 112 during respective portions of the scan, preprocesses the data and forwards the data to a display and/or processor for further processing and/or storage.

In operation, the NM portion of the scan may be conducted with rotor 104 rotationally powered separately from rotor 106. Each rotor may be controlled for each respective portion of the scan independently from the other rotor and may rotate about a respective NM viewing volume 814 and an x-ray viewing volume 816 simultaneously or sequentially during the scan. The NM portion of the scan may be conducted at a relatively low rotational speed, for example, three rotations per minutes. A computed tomography (CT) or x-ray portion of the scan may be conducted at a relatively higher rotational speed, for example three rotations per second. Motor 308 drives rotor 106 through belt 312 at the relatively high rotational speed during the CT portion of the scan. During the NM portion of the scan, a motor (not shown) drives rotor 104 at the relatively slower NM rotational speed. Either rotor may be selectively locked to stator 400 during a portion of the scan that the detectors associated with that rotor are not in use.

Each rotor may perform its associated portion of the scan simultaneously with the other rotor when performing its portion of the scan.

The above-described methods and systems for medical imaging using a multi-modality medical imaging system including an integrated gantry having a plurality of imaging detector rotors coupled to a single stator is cost-effective and highly reliable for imaging a patient. More specifically, the methods and systems described herein facilitate the benefits of multi-modality imaging in a system having a relatively small footprint. As a result, the methods and systems described herein facilitate imaging a patient in a cost-effective and reliable manner.

Exemplary embodiments of medical imaging systems and methods are described above in detail. The systems are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. A gantry assembly comprising:
   a stator;
   a first rotor rotatably coupled to said stator, said first rotor configured to rotate about an examination axis at a first rotational speed; and
   a second rotor rotatably coupled to at least one of said stator and said first rotor, said second rotor configured to rotate about the examination axis at the first rotational speed and a second rotational speed, said second rotational speed being greater than said first rotational speed, said first and second rotors configured to be locked in position with respect to each other during rotation at said first rotational speed, said first rotor configured to be locked in position with respect to said stator during rotation of said second rotor at said second rotational speed.

2. A gantry assembly in accordance with claim 1 wherein said stator further comprises a first stationary portion of a slip ring assembly.

3. A gantry assembly in accordance with claim 1 wherein said first rotor further comprises a first rotatable portion of said first slip ring assembly.

4. A gantry assembly in accordance with claim 1 wherein said second rotor further comprises a second rotatable portion of said first slip ring assembly.

5. A gantry assembly in accordance with claim 1 wherein said stator further comprises a stationary portion of a second slip ring assembly and said second rotor further comprises a first rotatable portion of said second slip ring assembly.

6. A gantry assembly in accordance with claim 1 wherein said stator further comprises a stationary portion of a main gantry bearing.

7. A gantry assembly in accordance with claim 6 wherein said stator further comprises a stationary portion of a first main gantry bearing, a rotating portion of said first main gantry bearing coupled to said first rotor.

8. A gantry assembly in accordance with claim 6 wherein said stator further comprises a stationary portion of a second main gantry bearing, a rotating portion of said second main gantry bearing coupled to said second rotor.

9. A gantry assembly in accordance with claim 6 wherein said main gantry bearing comprises:
   a first rotating portion coupled to said first rotor; and
   a second rotating portion coupled to said second rotor.

10. A gantry assembly in accordance with claim 1 wherein said first rotor is rotatably coupled to said stator through a first main gantry bearing, said second rotor is rotatably coupled to said first rotor through a second main gantry bearing.

11. A gantry assembly in accordance with claim 10 wherein said first and second rotors configured to co-rotate with respect to said stator at a first rotation speed, said first rotor configured to remain stationary when said second rotor is rotatable at said second rotatable speed.

12. A gantry assembly in accordance with claim 10 wherein said first rotor is selectably lockable to said second rotor during a first portion of a scan, said first rotor is selectably lockable to said stator during a second portion of a scan.

13. A gantry assembly in accordance with claim 1 wherein said first rotor further comprises at least one detector, said detector selectable between an operating position and a radially outer parked position.

14. A gantry assembly in accordance with claim 13 wherein said at least one detector comprises a detecting face, said detector configured to rotate about a swivel axis parallel to said examination axis.

15. A gantry assembly in accordance with claim 14 wherein said at least one detector is configured to rotate approximately 360 degrees about the swivel axis.

16. A gantry assembly in accordance with claim 15 wherein said at least one detector is configured to rotate approximately 180 degrees about the swivel axis between a detector face facing radially inwardly position to a detecting face facing radially outward position.

17. A gantry assembly in accordance with claim 13 wherein said at least one detector comprises two detectors configured to be oriented in an H-mode configuration wherein a detector face of each detector faces radially inwardly toward the examination axis and said detector faces are oriented substantially parallel with respect to each other.

18. A gantry assembly in accordance with claim 13 wherein said at least one detector comprises two detectors configured to be oriented in an L-mode configuration wherein a detector face of each detector faces radially inwardly toward the examination axis and said detector faces are oriented substantially perpendicular with respect to each other.

19. A gantry assembly in accordance with claim 1 wherein said second rotor is positioned in axial alignment with respect to said first rotor and positioned radially inward from said first rotor.

20. A gantry assembly in accordance with claim 1 wherein said second rotor is positioned axially offset with respect to said first rotor.

21. A gantry assembly in accordance with claim 20 wherein said first rotor is rotatably coupled to a first axial side of said stator and said second rotor is rotatably coupled to a second axial side of said stator.

22. A gantry assembly in accordance with claim 21 wherein said first rotor is rotatably coupled to a first axial side of said stator, said first rotor comprising a first detector that defines an first examination volume radially inward from said first detector, said second rotor rotatably coupled to a second axial side of said stator, said second rotor comprising a second detector that defines a second examination volume on an axially opposite side of said stator than said second rotor.

* * * * *